(12) United States Patent  
Carlino et al.

(10) Patent No.: US 8,754,128 B2  
(45) Date of Patent: Jun. 17, 2014

(54) DIOXOANTHRACENE SULPHONATE DERIVATIVES

(75) Inventors: Stefano Carlino, Collombey (CH); Alessandro Di Napoli, Collonge-Bellerive (CH)

(73) Assignee: Laboratoire Medidom SA, Sarnen (CH)

( * ) Notice: Subject to any disclaimer, the term of this patent is extended or adjusted under 35 U.S.C. 154(b) by 577 days.

(21) Appl. No.: 12/743,212

(22) PCT Filed: Nov. 14, 2008

(86) PCT No.: PCT/IB2008/054777  
§ 371 (c)(1), (2), (4) Date: May 14, 2010

(87) PCT Pub. No.: WO2009/063427  
PCT Pub. Date: May 22, 2009

(65) Prior Publication Data  
US 2011/0054032 A1    Mar. 3, 2011

(30) Foreign Application Priority Data

Nov. 16, 2007 (EP) .................... 07022268

(51) Int. Cl.
| | | |
|---|---|---|
| *A01N 37/10* | (2006.01) | |
| *A61K 31/19* | (2006.01) | |
| *C07C 309/00* | (2006.01) | |
| *C07C 309/60* | (2006.01) | |

(52) U.S. Cl.
CPC .................. *C07C 309/60* (2013.01)
USPC .......................... 514/570; 562/53

(58) Field of Classification Search
CPC .................................................... C07C 309/60
See application file for complete search history.

(56) References Cited

U.S. PATENT DOCUMENTS

| | | | |
|---|---|---|---|
| 4,244,968 A | 1/1981 | Friedmann | |
| 6,124,358 A * | 9/2000 | Estanove et al. | 514/548 |
| 6,797,727 B2 * | 9/2004 | Cruz et al. | 514/510 |

FOREIGN PATENT DOCUMENTS

| | | |
|---|---|---|
| EP | 0 570 091 A1 | 11/1993 |
| JP | H 07285855 A | 10/1995 |
| WO | 02058681 A2 | 8/2002 |
| WO | WO 02/07639 A2 | 10/2002 |

OTHER PUBLICATIONS

Burger et al. Is IL-I a good therapeutic target in the treatment of arthritis? Best Practice & Research Clinical Rheumatology, vol. 20, No. 5, pp. 879-896, 2006.*
English translation of Japanese Examination Report dated Jul. 18, 2013, for JP 2010 533705; 4 pages.

* cited by examiner

*Primary Examiner* — Anna Pagonakis
(74) *Attorney, Agent, or Firm* — Faegre Baker Daniels LLP

(57) ABSTRACT

Compounds that may have anti-inflammatory activity have the general formula (I): Wherein $R_1$, $R_2$, $R_3$ are each independently H or a $C_{1-4}$ alkyl group or a $C_{2-4}$ acyl group; $R_4$ and $R_5$ are each independently H or a group of formula —$SO_3R_6$, wherein $R_6$ is H or a $C_{1-4}$ alkyl group or a $C_{2-4}$ acyl group; with the proviso that at least one of $R_4$ and $R_5$ is a group of formula —$SO_3R_6$, or a pharmaceutically acceptable salt thereof.

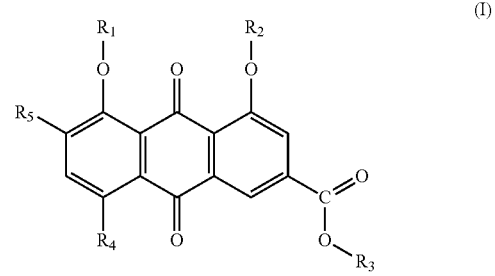

(I)

25 Claims, 5 Drawing Sheets

DIOXOANTHRACENE SULPHONATE DERIVATIVES

The present invention relates to certain dioxoanthracene sulphonate derivatives, to a process for the preparation thereof, and to the use of the compound as a medicament, particularly in the therapy of conditions that are influenced by pro-inflammatory cytokines of the IL-1 family, particularly inflammatory and auto-immune diseases, for instance arthritic diseases.

Rhein, 4,5-dihydroxy-9,10-dioxo-2-anthracene carboxylic acid, and its diacetylated derivative diacerein, are known for a number of pharmaceutical applications. Particularly rhein and diacerein are known for use in the treatment of arthritic diseases, in particular osteoarthritis and rheumatoid arthritis, for instance as described in U.S. Pat. No. 4,244,968, GB 1 578 452, EP 544 880 B1, EP 636 602 B1 and U.S. Pat. No. 6,610,750, and psoriaris and associated conditions, as described in EP 1 248 608 B1. Rhein and diacerein have also been described for the treatment of various conditions, for instance inflammatory diseases, auto-immune diseases, vascular diseases, pain relief, diabetic nephrosis.

The cytokines IL-1 ($\alpha$, $\beta$) and TNF-$\alpha$ are considered to play an essential role in the mediation of the inflammatory process and cartilage degradation. IL-1 and TNF-$\alpha$ are also considered to be implicated in the mediation of biological responses to endotoxins and other infectious stimuli. An extensive review of pro-inflammatory and anti-inflammatory cytokines is given by C. A. Dinarello, MD et L. L. Moldawer, PhD in the primer for clinicians *"Proinflammatory and Anitinflammatory Cytokines in Rheumatoid Arthritis"*, 2000, Amgen Inc. The cytokines IL-1 and TNF-$\alpha$ have been implicated in the mechanism of a number of inflammatory and auto-immune conditions such as osteoarthritis, rheumatoid arthritis, psoriatic arthritis, psoriaris, Paget's disease, osteoporosis, inflammatory bowl diseases including ulcerative colitis and Crohn's disease, endometriosis, Wegener's granulomatosis, neurological dysfunctions such as Alzheimer's disease and Parkinson's disease, myeloma, myeloid leukaemia, bone metastasis, diabetic nephrosis, chronic heart disease, arthrosclerosis, asthma.

Diacerein and its active metabolite rhein are known to inhibit the synthesis and activity of pro-inflammatory catabolic cytokines of the interleukin-1 (IL-1) family, particularly IL-1$\beta$. Rhein and diacerein have been shown to inhibit expression of IL-6, IL-8 and other cytokines such as tissue necrosis factor (TNF-$\alpha$). Inhibition of inflammatory cytokines IL-1 and TNF-$\alpha$ by rhein and diacerein is described, for instance, in WO 02/058681, WO 01/051044, J. Martel-Pelletier et al. *Journal of Rheumatology*, 1998, 25 (4), 753-762, E. Douni et al. *Arthritis Res Ther*, 2004, 6: R65-R72.

Chondrocytes from patients suffering from these conditions express high levels of TNF-$\alpha$ and IL-1, compared to chondrocytes from healthy individuals, and this specific mechanism of action of rhein as an IL-1 inhibitor is believed to explain, at least in part, the effectiveness of rhein and diacerein in the treatment of certain arthritic conditions, for instance, rheumatoid arthritis, osteoarthritis and psoriatic arthritis.

The metabolite Aloe-emodin present in diacerein has, however, been shown to have clastogenic effect in colon and kidney cells. Genotoxicity of *Aloe*-emodin, tested by Comet assay, is reported, for instance, by S. O. Müller et al., *Mutation Research*, 371, (1996), 165-173.

Further, rhein and diacerein have the drawback of being poorly soluble in aqueous solution, making the preparation of pharmaceutical dosage forms, from which the therapeutic agent is bioavailable, difficult. The poor solubility of rhein and diacerein is a particular problem with respect to formulations for parenteral administration.

Diacerein, and its active metabolite rhein, are known to have a tendency to produce laxative effects in patients over long-term treatment. It is believed that this laxative effect may be attributed, at least in part, to the very poor solubility of rhein and diacerein.

There is an ongoing need to provide further compounds for the treatment or therapy of conditions that are influenced or mediated by pro-inflammatory cytokines of the IL-1 family, particularly inflammatory and auto-immune diseases, including arthritic diseases.

It would further be advantageous to provide alternative compounds having activity for the inhibition of pro-inflammatory cytokines of the IL-1 family, and which allow to address certain drawbacks of rhein and/or diacerein.

It would be further advantageous to provide compound having improved activity for the inhibition of pro-inflammatory cytokines of the IL-1 family.

There are now provided novel pharmaceutical compounds of the formula (I):

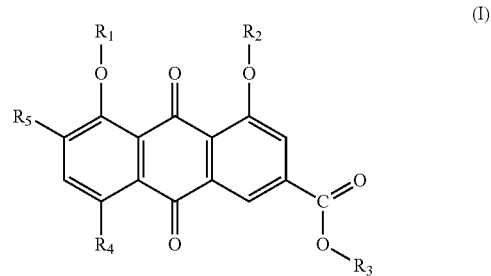

wherein $R_1$, $R_2$, $R_3$ are each independently H or a $C_{1-4}$ alkyl group or a $C_{2-4}$ acyl group;
$R_4$ and $R_5$ are each independently H or a group of formula —$SO_3R_6$, wherein $R_6$ is H or a $C_{1-4}$ alkyl group or a $C_{2-4}$ acyl group;
with the proviso that at least one of $R_4$ and $R_5$ is a group of formula —$SO_3R_6$.

According to a particular embodiment of the present invention there is provided a compound of the formula (I) wherein $R_1$, $R_2$, $R_3$ and $R_4$ are H, and $R_5$ is —$SO_3H$ (formula (III)).

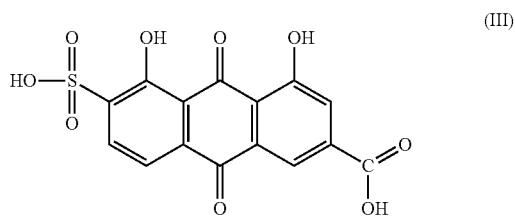 [SMILES: O=C(O)c1cc(O)c2c(c1)C(=O)c1ccc(S(=O)(=O)O)c(O)c1C2=O]

It has unexpectedly been found by the inventors that compounds of the formula (I) are capable of inhibiting production of pro-inflammatory cytokines of the IL-1 family. Compounds of formula (I) wherein $R_4$ and/or $R_5$ is —$SO_3H$ have also been shown to exhibit advantageous solubility properties.

According to one aspect of the present invention there is provided a process for the preparation of a compound of formula (I), which comprises treating the corresponding compound of formula (II):

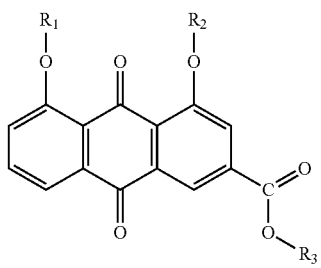

Wherein $R_1$, $R_2$ and $R_3$ are each independently H, with sulphuric acid.

According to one aspect of the invention there is now provided a pharmaceutical composition comprising a compound of formula (I) in combination with suitable pharmaceutically acceptable excipients.

According to further aspects, the present invention relates to a compound of formula (I) for use as a medicament for human or veterinary application, to a compound of formula (I) for the treatment of conditions that are mediated or influenced by cytokines of the IL-1 family, particularly for the treatment of inflammatory or auto-immune diseases, to the use of a compound of formula (I) for the preparation of a medicament for the treatment of conditions that are mediated or influenced by cytokines of the IL-1 family, particularly inflammatory or auto-immune diseases, and to a method for the treatment of a condition mediated or influenced by cytokines of the IL-1 family, which comprises administering to a subject a therapeutically effective amount of a compound of formula (I).

Other objects and advantages of the present invention will be apparent from the claims and the following detailed description, examples and accompanying drawings.

FIGS. 1(a), 1(b) and 1(c) show the $^1$H-NMR spectra of a compound according to the present invention;

Figure 1A:
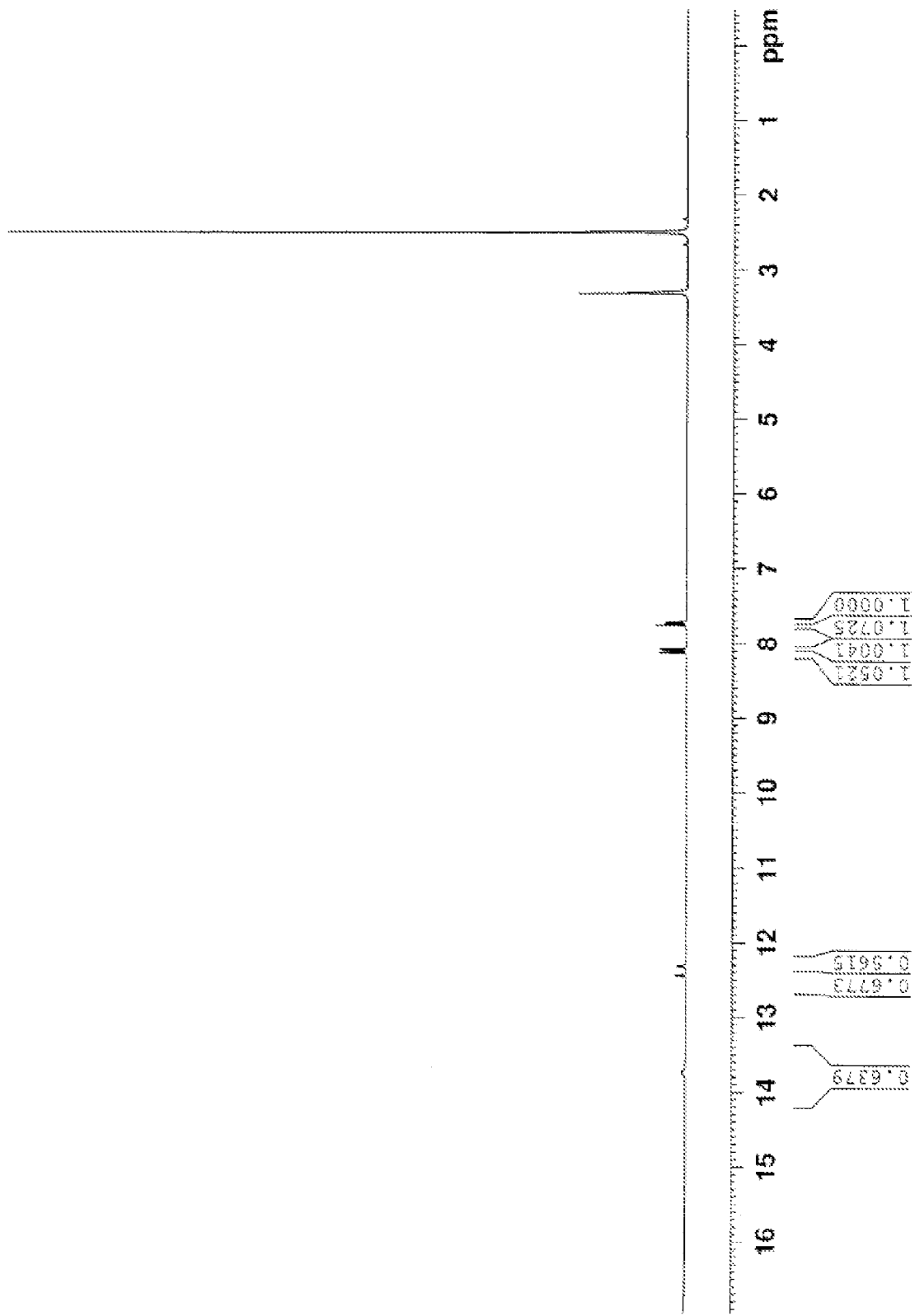

The present invention provides a compound of the formula (I):

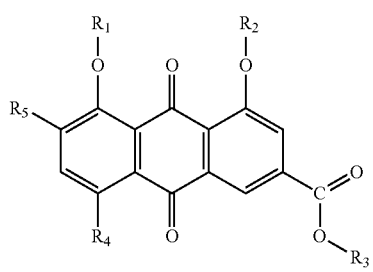

Wherein $R_1$, $R_2$, $R_3$ are each independently H or a $C_{1-4}$ alkyl group or a $C_{2-4}$ acyl group;

$R_4$ and $R_5$ are each independently H or a group of formula —$SO_3R_6$, wherein $R_6$ is H or a $C_{1-4}$ alkyl group or a $C_{2-4}$ acyl group;

with the proviso that at least one of $R_4$ and $R_5$ is a group of formula —$SO_3R_6$.

According to one embodiment of the invention $R_1$ and $R_2$ are independently selected from H, a $C_{1-4}$ alkyl group or a $C_{2-4}$ acyl group; $R_3$ is H, and $R_4$ and $R_5$ may be H or —$SO_3H$, with the proviso that at least one of $R_4$ and $R_5$ is —$SO_3H$. In a preferred embodiment, $R_1$ and $R_2$ are either both H or both acetyl groups, $R_3$ and $R_4$ are both H, and $R_5$ is —$SO_3H$.

According to one embodiment of the invention $R_1$, $R_2$, $R_3$ are H, and $R_4$ and $R_5$ are independently H or —$SO_3H$, with the proviso that at least one of $R_4$ and $R_5$ is —$SO_3H$.

According to a preferred embodiment of the present invention there is provided a compound of the formula (III) (6-sulfo-4,5-dihydroxy-9,10-dioxo-2-anthracene carboxylic acid):

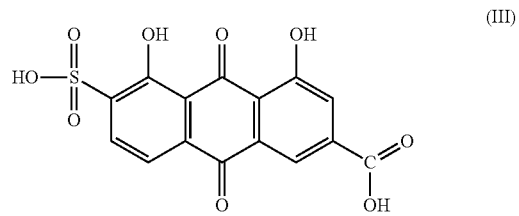 [SMILES: O=C(O)c1cc(O)c2c(c1)C(=O)c1ccc(S(=O)(=O)O)c(O)c1C2=O]

The compounds of the present invention may be in the form of a pharmaceutically acceptable salt thereof. Particularly sodium, potassium or ammonium salts are contemplated.

Compounds of formula (I) may be prepared by a process according to the present invention, which comprises treating a compound of formula (II)

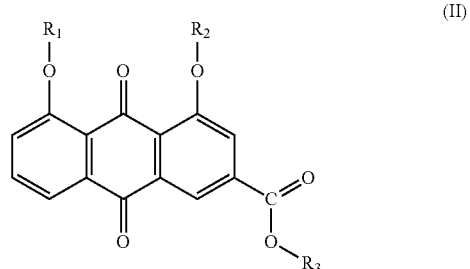

in which $R_1$, $R_2$ and $R_3$ are H, with concentrated sulphuric acid to produce the corresponding compound of formula (I), in the form of the sulphonic acid. In a further step desired $C_{1-4}$ alkyl group or a $C_{2-4}$ acyl group can be selectively substituted using conventional techniques. For instance, reaction with a $C_{2-4}$ acyl halide, or corresponding acyl anhydride, to introduce the desired $C_{2-4}$ acyloxy group, reaction with a $C_{1-4}$ alcohol to form the corresponding ester, or for instance reaction with diazomethane ($CH_2N_2$) to introduce $C_1$ alkyl group or with a $C_{2-4}$ alkyl halide to introduce the corresponding $C_{2-4}$ alkyl group. Depending on the desired substitution, known protecting groups may be introduced, where necessary, and cleaved using conventional processes.

Alternatively, sulphuric acid can be replaced with pyrosulphuric acid.

The reaction with sulphuric acid is preferably carried out at a temperature between 60 and 120° C., preferably around 100° C.

The reaction time with the acid may vary, dependent for instance on the reaction temperature, the acid used, the desired product (i.e. di- or mono-sulphonic acid substitution) etc. As a general indication reaction times of between 1 hour and 48 hours may be envisaged, for instance around 24 hours. The progress of the reaction may advantageously be monitored, for example by HPLC, and the reaction stopped at completion of the reaction to the desired di- or mono-sulphonate substituted product.

The product may be isolated in the form of its corresponding salt, for instance by addition of the corresponding metal halide (e.g. NaCl), or the corresponding metal alkalizing agent (such as NaOH, KOH or $NH_3$). Salts envisaged include any pharmaceutically acceptable salt, such as, for instance, sodium, potassium or ammonium.

The thus obtained compound of formula (I) may be purified using any suitable conventional purification process, such as, for instance, preparative HPLC or liquid-liquid partitioning.

Compounds of formula (I) according to the present invention exhibit activity in the inhibition of pro-inflammatory cytokines of the IL-1 family.

In in-vitro studies in human chondrocytes, compounds of formula (I) have unexpectedly been shown to exhibit improved inhibition of interleukin-1 (IL-1β), compared to rhein.

Advantageously, compounds of formula (I) can allow to avoid the metabolite aloe-emodin, present in diacerein.

In view of their activity in the inhibition of pro-inflammatory cytokines of the IL-1 family, compounds of the present invention are contemplated for the treatment of conditions characterised by an abnormally high or increased level of IL-1.

The conditions that may be treated with compounds of the present invention include inflammatory and auto-immune diseases. Conditions that may be mentioned include rheumatoid arthritis, osteoarthritis, osteoporosis, psoriatic arthritis, psoriaris, arthrosclerosis, Paget's disease, chronic heart disease, inflammatory bowel diseases including ulcerative colitis and Crohn's disease, endometriosis, Wegener's granulomatosis, neurological dysfunctions such as Alzheimer's disease and Parkinson's disease, myeloma, myeloid leukaemia, bone metastasis, diabetic nephrosis, pneumonary emphysema, asthma.

Accordingly, one aspect of the present invention relates to a method of treating conditions characterised by increased levels of IL-1, as compared to healthy individuals, which comprises administering to a subject an effective amount of a compound according to the present invention or a pharmaceutically acceptable salt thereof. The conditions are preferably inflammatory diseases or auto-immune diseases. Particularly the conditions to be treated include inflammatory diseases of the joints in particular osteoarthritis or rheumatoid arthritis. Psoriatic arthritis and psoriaris may also be particularly mentioned.

It is likely that the compounds of the present invention will be of clinical utility in the wide range of inflammatory and auto-immune diseases described above, due also to their improved physical properties compared with rhein.

According to one aspect of the invention there is provided a pharmaceutical composition comprising the compound of formula (I) in combination with suitable pharmaceutically acceptable excipients. Pharmaceutical compositions according to the present invention may be for human or veterinary use.

The pharmaceutical compositions according to the present invention may have a formulation suitable for administration by any route, including, for example, oral, intramuscular, intravenous, subcutaneous, rectal, topical, transcutaneous, intranasal, intrarticular, sublingual and intraperitoneal administration.

Formulations for oral administration may include, for instance, tablets, hard or soft gelatin capsules, lozenges, aqueous or oily suspensions, dispersible powders or granules for reconstitution, syrups or emulsions.

Formulations for parenteral administration may be in any suitable pharmaceutical form, such as in the form of a sterile injectable aqueous buffered solution or suspension, as a sterile injectable solution or suspension in any other non-toxic parenterally acceptable diluent or solvent, or in a freeze-dried form for reconstitution at the time of use.

The compositions of the present invention may be also be provided in formulations for topical administration, for instance in the form of a cream, gel, ointment or emulsion in an aqueous or oily carrier.

Compounds of formula (I) according to the present invention are expected to show better solubility in water than rhein or diacerein due to the presence of the sulphonate group. For instance, compounds of formula (I) according to the present invention wherein $R_1$, $R_2$, $R_3$ are H and $R_4$ and $R_5$ are independently or both $SO_3H$, have been shown to exhibit particularly good solubility in aqueous solution. For example, the compound of formula (III) has a solubility in water of 1.2 mg/ml while rhein and diacerein are practically insoluble in water.

The good solubility properties of the compounds of the present invention allows the compounds to be advantageously administered by parenteral routes, e.g. by injection or infusion, particularly as intraarticular, intramuscular, intravenous or subcutaneous injection or infusion.

The pharmaceutical compositions may be prepared according to methods known in the art, using suitable known pharmaceutically excipients and/or additives.

Any suitable conventional pharmaceutically acceptable excipients are contemplated, for example diluents, binders, surfactants, lubricants, suspending agents, emulsifiers, buffers anticaking agents, aqueous or oily carriers, disintegrating agents, preserving agents, flavouring agents, sweetening agents, colouring agents, in accordance with the selected route of administration.

Suitable dosage regimes will vary dependent, amongst other things, on factors such as the therapeutic application, the severity of the condition and with respect to the patient to be treated. Typical daily dosage amounts may vary in the order of from about 0.05 mg to about 150 mg per kg of patient bodyweight per day. In general terms a daily dosage of from about 10 mg to 500 mg per day, such as between about 10 mg and about 250 mg per day may be envisaged. The amount of active ingredient in a unit dosage from will depend on the above factors and also on the chosen route of administration, and will generally be in the region of 1 mg to 500 mg of active ingredient per unit dosage form.

The invention is further illustrated by the following-non limiting examples.

EXAMPLES

Example 1

Preparation of 6-sulfo-4,5-dihydroxy-9,10-dioxo-2-anthracene carboxylic acid

Rhein (1 g) produced by the deacetylation of pure diacerein, having a purity more than 99%, was dissolved in concentrated sulphuric acid (100 ml). The solution was heated at 100° C. and stirred for 24 hours. Progress of the reaction was followed in real time using HPLC to completion of the reaction. The reaction mixture was then allowed to cool and poured into 2 l water with stirring. The resultant solution was then stored over the night at 4° C. The unreacted rhein salting material was eliminated by centrifuge. The compound 6-sulfo-4,5-dihydroxy-9,10-dioxo-2-anthracene carboxylic acid was precipitated as its sodium salt by the addition of 110 g of sodium chloride. The resulting suspension was cooled at 4° C. for one hour, then centrifuged to separate out the solid product and dried under vacuum. 2.32 g of product was obtained.

Elimination of Salts:

The product obtained above was added to water (115 ml) with mixing at 4° C. for 30 minutes. The suspension was then centrifuged and decanted to eliminate the supernatant with the residual salts. This operation was repeated seven times until a constant conductivity (around 330 µS/cm), measured with a conductivity meter (Radiometer CDM 206). The residue after centrifuging was then dried under vacuum to obtain 480 mg of product, with a purity of 95.6% as determined by HPLC.

Example 2

Figure 1B:
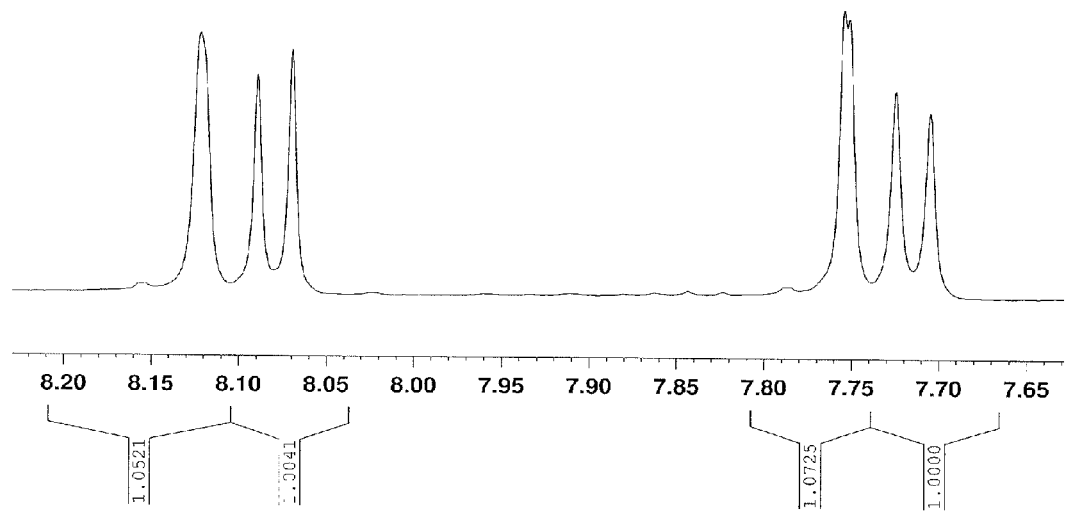
Figure 1C:
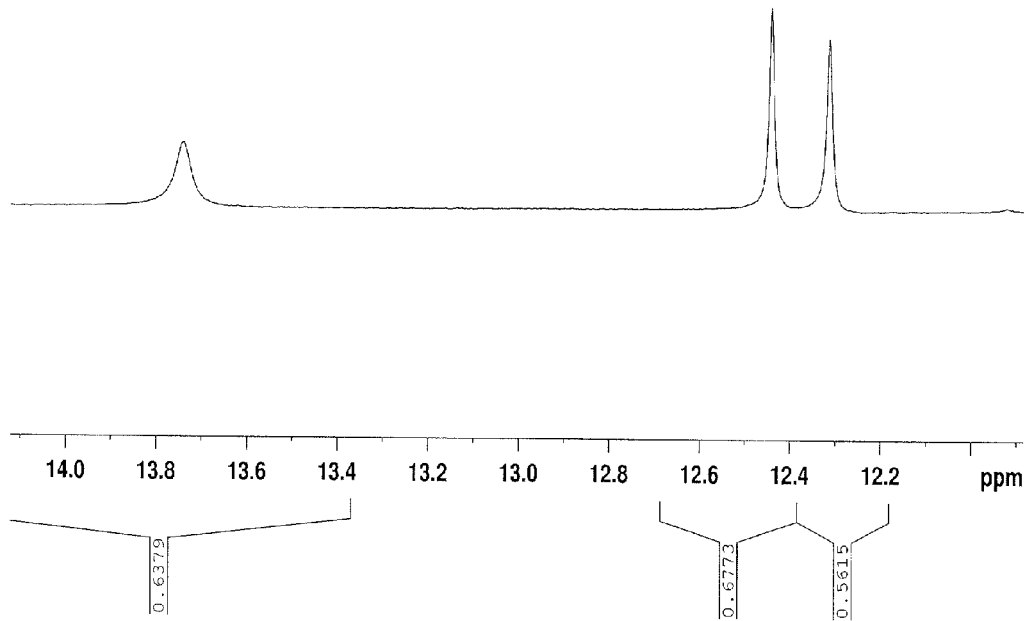

Characterization $^1$H-NMR Analysis:

$^1$H-NMR spectrum of the product obtained in example 1 was carried out in dimethyl sulphoxide (DMSO) using a Bruker® spectrometer at 400 MHz. The spectra obtained, shown in FIGS. 1(a) to 1(c), shows concordance with the product 6-sulfo-4,5-dihydroxy-9,10-dioxo-2-anthracene carboxylic acid.

The $^1$H-NMR spectra indicates the presence of only four aromatic protons, two in the meta position and two in ortho positions. Showing that the sulphonic acid substitution has occurred in the ring which previously had only a hydroxyl substituent. The chemical displacements (shifts), compared to caculated chemical displacements on the basis of increments, show the substitution of the sulphonic acid group to be in the ortho position.

Figure 2:
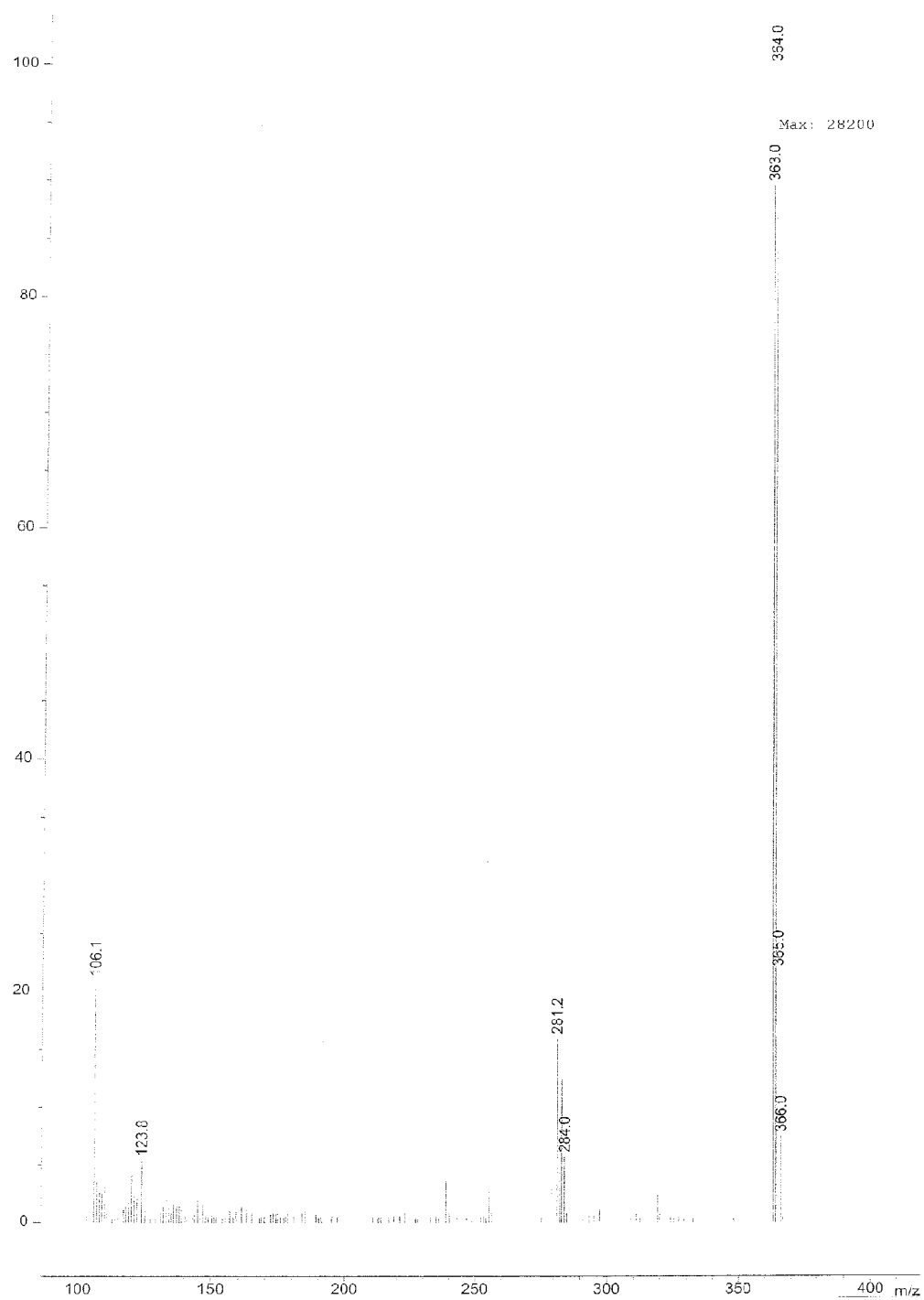
FIG. 2 shows the MS analysis of the same compound according to the present invention.

MS Analysis:

Mass spectroscopy carried out on the product of example 1 with an Agilent 1100 LC-MS Spectrometer, with ionisation at atmospheric pressure in negative eletro-spray mode. The spectrum obtained, shown in FIG. 2, shows a peak at 364, and thus concords with the product 6-sulfo-4,5-dihydroxy-9,10-dioxo-2-anthracene carboxylic acid, formula (III).

Example 3

Preparation of 6-sulfo-4,5-dihydroxy-9,10-dioxo-2-anthracene carboxylic acid sodium salt Rhein (1 g) produced by the deacetylation of pure diacerein, having a purity more than 99%, was dissolved in concentrated sulphuric acid (100 ml). The solution was heated at 100° C. and stirred for 24 hours. Progress of the reaction was followed in real time using HPLC to completion of the reaction. The reaction mixture was then allowed to cool and poured into 2 l water with stirring. The resultant solution was then stored over the night at 4° C. The unreacted rhein salting material was eliminated by centrifuge. The pH of the surnatant was adjusted to 7.0 with NaOH 1M. The product 6-sulfo-4,5-dihydroxy-9,10-dioxo-2-anthracene carboxylic acid, in the form of its sodium salt, was then isolated and purified from the solution by preparative HPLC using a reversed phase C18 silica column and methanol/water/$H_3PO_4$ eluent. 1 g of product was isolated and characterised as 6-sulfo-4,5-dihydroxy-9,10-dioxo-2-anthracene carboxylic acid sodium salt by NMR and MS as in example 2.

Example 4

In Vitro Studies on IL-1β Inhibition in Human Chondrocytes

The activity of the compound of example 1, and of rhein in inhibiting the lipopolysaccharide (LPS) stimulated production of IL-1 β cytokine by human normal and osteoarthritic (OA) chondrocytes was studied.

Materials and Methods:

Human cartilage was obtained during orthopaedic surgery for total hip prosthesis due to traumatic fracture in normal subjects or OA patients. Patients with OA were selected on the basis of the following criteria (1) bi-lateral OA, (2) diagnoses of moderate OA (grade I-III, Kellgren-Laurence), supported by radiology and pathology.

A suspension of isolated chondrocytes was prepared from cartilage specimens obtained from four OA patient and nine normal subjects. Specimens were obtained and maintained under aseptic conditions. The cartilage was cut into small fragments and incubated with 1 mg/ml clostridial collagenase in carbonate/bicarbonate buffer for 48 hours at 37° C. Once separated from the cartilage matrix, chondrocytes were centrifuged at 1500 RPM for five minutes. The separated chondrocytes, suspended in culture medium (DMEM supplemented with 10% SCF) were used for the experiment. Cell viability was evaluated by Trypan blue exclusion.

In vitro stimulation of chondrocytes with bacterial endotoxin (LPS) for the production of IL-1 β was carried out as follows:

Aliquots of 1×10$^6$ cells/ml in culture medium were seeded in 15 ml Falcon tubes and maintained under agitation on a gyratory shaker (100 RPM).

Chondrocytes were cultured for 48 hours in the presence of MPS (10 µg/ml) with 20 mg/ml rhein, or increasing concentrations (1, 5, 10, 20 and 30 µg/ml) of the test compound (compound of Example 1). For the samples with rhein the solution was subjected to five minutes sonication in order to minimize solubility problems related to the hydrophobic nature of rhein. This problem was not present for the solutions of the test compound due to its good solubility.

IL-1β production by chondrocytes was assayed in the culture medium in the various sample cultures by an ELISA kit.

Figure 3:
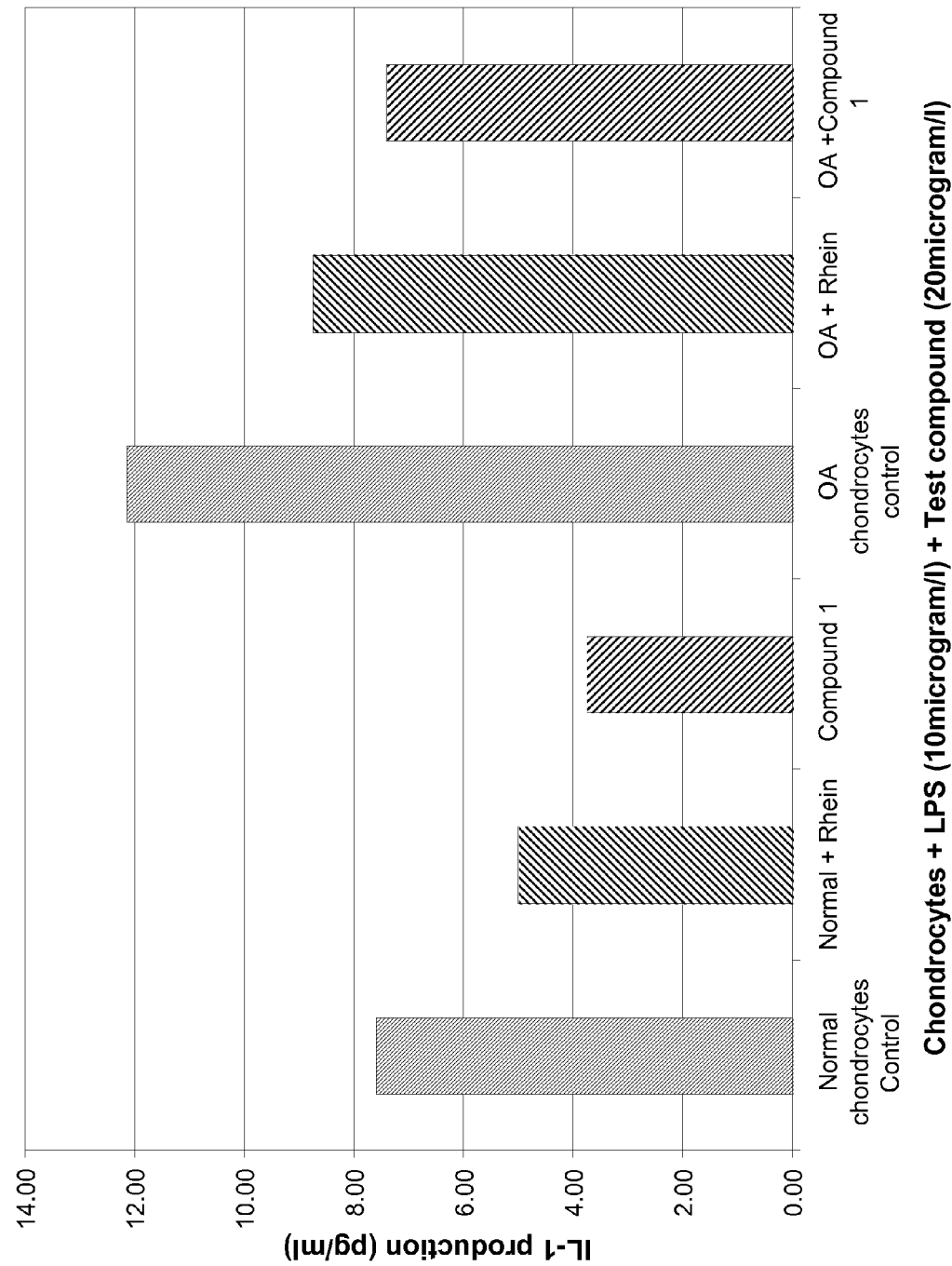
FIG. 3 is a graphical representation showing the effects of a compound according to the present invention on the inhibition of IL-1 β cytokine production in human chondrocytes.
Figure 4:
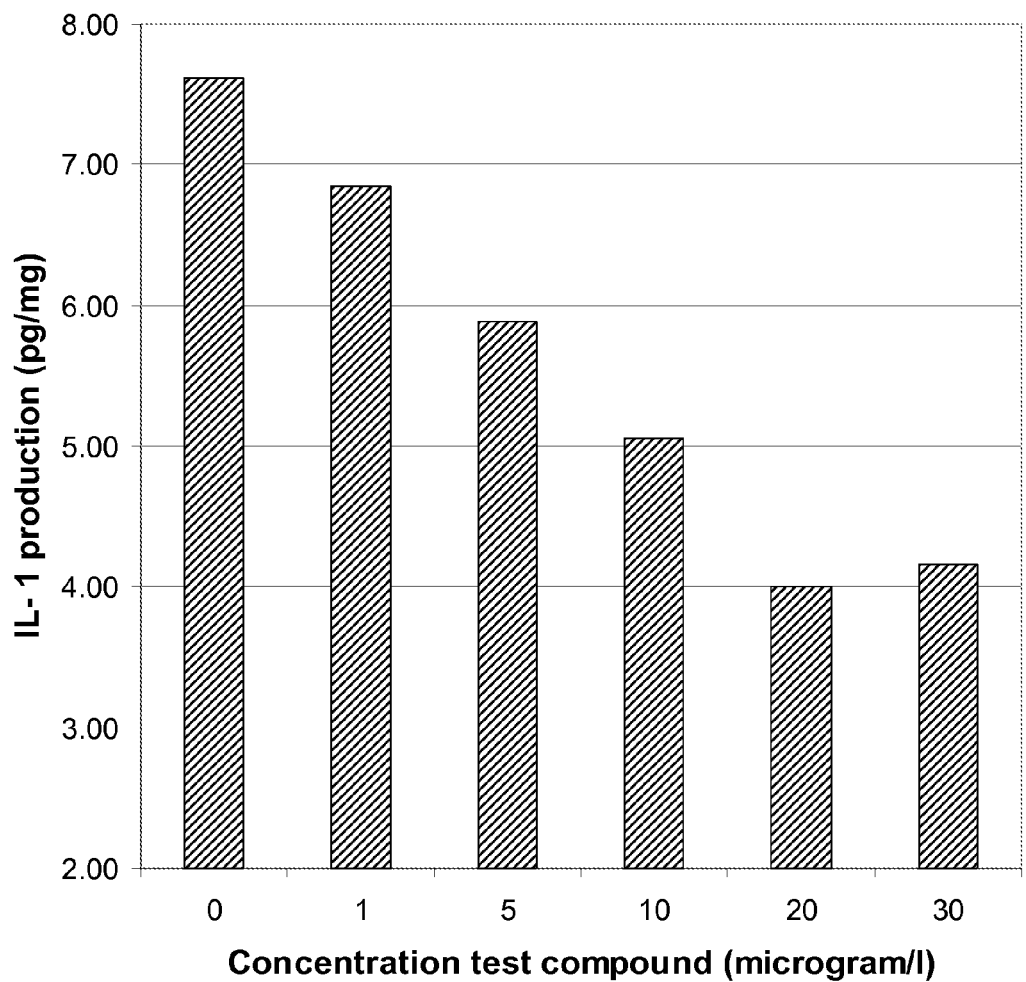
FIG. 4 is a graphical representation showing the dose-dependent inhibition of IL-1 β cytokine production in human chondrocytes by a compound according to the present invention.

FIG. 3 shows the results obtained with rhein and the compound of Example 1 on IL-1β production in LPS-stimulated normal and OA chondrocytes, as evaluated by ELISA. FIG. 4 shows the dose-dependent inhibition of IL-1βproduction of normal chondrocytes by the test compound (compound of Example 1). The results illustrated in FIG. 3 show the compound of the present invention to exhibit significantly increased IL-1β inhibition activity compared with rhein. FIG. 4 shows the compound according to the invention to provide significant inhibition of IL-1β production, with maximum inhibition between 10 and 20 mg/ml.

What is claimed is:

1. A compound of the formula (I):

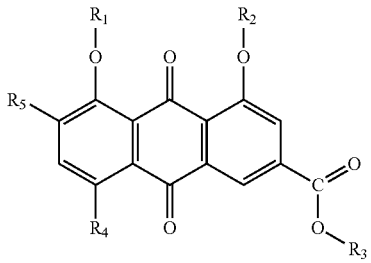

wherein $R_1$, $R_2$, $R_3$ are each independently H or a $C_{1-4}$ alkyl group or a $C_{2-4}$ acyl group;
$R_4$ and $R_5$ are each independently H or a group of formula —$SO_3R_6$, wherein $R_6$ is H or a $C_{1-4}$ alkyl group or a $C_{2-4}$ acyl group;
with the proviso that at least one of $R_4$ and $R_5$ is a group of formula —$SO_3R_6$, or a pharmaceutically acceptable salt thereof.

2. The pharmaceutical composition comprising a compound according to claim 1, or a pharmaceutically acceptable salt thereof, as an active ingredient.

3. The pharmaceutical composition according to claim 2, wherein the composition is for parenteral administration.

4. The pharmaceutical composition according to claim 2, wherein the composition is for oral administration.

5. The pharmaceutical composition according to claim 2, wherein the composition is for topical administration.

6. A method for the treatment of a disease mediated or influenced by pro-inflammatory cytokines of the IL-1 family, said disease being an arthritic disease, which comprises administering to a subject a therapeutically effective amount of a compound according to claim 1, or a pharmaceutically acceptable salt thereof.

7. A method for the treatment of an inflammatory or auto-immune disease, said disease being an arthritic disease, which comprises administering to a subject a therapeutically effective amount of a compound according to claim 1, or a pharmaceutically acceptable salt thereof.

8. The method according to claim 6 wherein the disease is selected from osteoarthritis, rheumatoid arthritis, psoriatic arthritis or psoriasis.

9. A method for the preparation of a compound of formula (I):

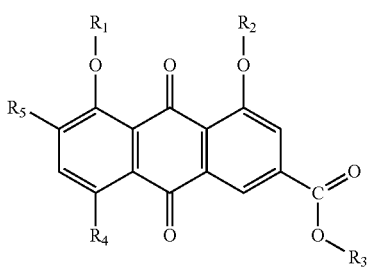

wherein $R_1$, $R_2$, $R_3$ are each independently H or a $C_{1-4}$ alkyl group or a $C_{2-4}$ acyl group;
$R_4$ and $R_5$ are each independently H or a group of formula —$SO_3R_6$, wherein $R_6$ is H or a $C_{1-4}$ alkyl group or a $C_{2-4}$ acyl group;
with the proviso that at least one of $R_4$ and $R_5$ is a group of formula —$SO_3R_6$
or a pharmaceutically acceptable salt thereof,
comprising treating the compound of formula (II)

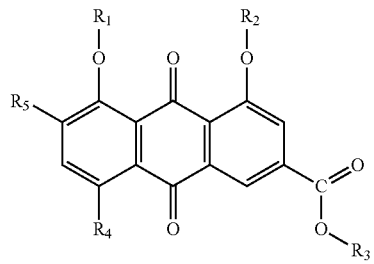

wherein $R_1$, $R_2$, $R_3$ are H, with concentrated sulphuric acid.

10. A compound of the formula (I)

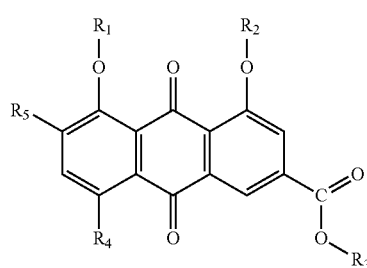

wherein $R_1$, $R_2$ are independently H or a $C_{1-4}$ alkyl group or a $C_{2-4}$ acyl group, $R_3$ and $R_4$ are H, and $R_5$ is —$SO_3H$.

11. The pharmaceutical composition comprising a compound according to claim 10, or a pharmaceutically acceptable salt thereof, as an active ingredient.

12. The pharmaceutical composition according to claim 11, wherein the composition is for parenteral administration.

13. The pharmaceutical composition according to claim 11, wherein the composition is for oral administration.

14. The pharmaceutical composition according to claim 11, wherein the composition is for topical administration.

15. A method for the treatment of a disease mediated or influenced by pro-inflammatory cytokines of the IL-1 family, said disease being an arthritic disease, which comprises administering to a subject a therapeutically effective amount of a compound according to claim 10, or a pharmaceutically acceptable salt thereof.

16. A method for the treatment of an inflammatory or auto-immune disease, said disease being an arthritic disease, which comprises administering to a subject a therapeutically effective amount of a compound according to claim 10, or a pharmaceutically acceptable salt thereof.

17. The method according to claim 15 wherein the disease is selected from osteoarthritis, rheumatoid arthritis, psoriatic arthritis or psoriasis.

18. A compound having the formula (III):

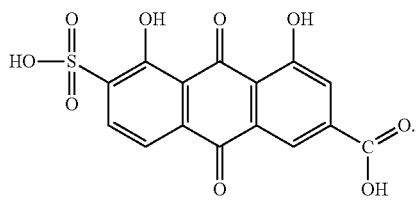 [SMILES: O=C(O)c1cc(O)c2c(c1)C(=O)c1ccc(S(=O)(=O)O)c(O)c1C2=O]

19. The pharmaceutical composition comprising a compound according to claim 18, or a pharmaceutically acceptable salt thereof, as an active ingredient.

20. The pharmaceutical composition according to claim 19, wherein the composition is for parenteral administration.

21. The pharmaceutical composition according to claim 19, wherein the composition is for oral administration.

22. The pharmaceutical composition according to claim 19, wherein the composition is for topical administration.

23. A method for the treatment of a disease mediated or influenced by pro-inflammatory cytokines of the IL-1 family, said disease being an arthritic disease, which comprises administering to a subject a therapeutically effective amount of a compound according to claim 18, or a pharmaceutically acceptable salt thereof.

24. A method for the treatment of an inflammatory or auto-immune disease, said disease being an arthritic disease, which comprises administering to a subject a therapeutically effective amount of a compound according to claim 18, or a pharmaceutically acceptable salt thereof.

25. The method according to claim 23 wherein the disease is selected from osteoarthritis, rheumatoid arthritis, psoriatic arthritis or psoriasis.

* * * * *